US009404871B2

(12) United States Patent
Delmonico

(10) Patent No.: US 9,404,871 B2
(45) Date of Patent: Aug. 2, 2016

(54) METHOD AND SYSTEM FOR STEERING AN INSERTION TUBE OF A VIDEO INSPECTION DEVICE

(75) Inventor: James Jonathan Delmonico, Baldwinsville, NY (US)

(73) Assignee: General Electric Company, Schenectady, NY (US)

( * ) Notice: Subject to any disclaimer, the term of this patent is extended or adjusted under 35 U.S.C. 154(b) by 815 days.

(21) Appl. No.: 13/346,328

(22) Filed: Jan. 9, 2012

(65) Prior Publication Data

US 2013/0176417 A1 Jul. 11, 2013

(51) Int. Cl.

| | |
|---|---|
| ***H04N 9/47*** | (2006.01) |
| ***H04N 7/18*** | (2006.01) |
| ***G01N 21/88*** | (2006.01) |
| ***F01D 17/02*** | (2006.01) |
| ***F01D 17/20*** | (2006.01) |

(52) U.S. Cl.

CPC ............ *G01N 21/8806* (2013.01); *F01D 17/02* (2013.01); *F01D 17/20* (2013.01)

(58) Field of Classification Search

CPC ................... H04N 2005/2255; G01N 21/8806

USPC ............................................................ 348/82

See application file for complete search history.

(56) References Cited

U.S. PATENT DOCUMENTS

| | | | | |
|---|---|---|---|---|
| 4,941,454 | A | 7/1990 | Wood et al. | |
| 5,373,317 | A | 12/1994 | Salvati et al. | |
| 5,417,210 | A * | 5/1995 | Funda et al. | 600/425 |
| 6,208,328 | B1 * | 3/2001 | Kawachiya et al. | 345/157 |
| 7,557,794 | B2 * | 7/2009 | Rosenberg et al. | 345/156 |
| 2007/0156017 | A1 * | 7/2007 | Lamprecht et al. | 600/102 |
| 2007/0217777 | A1 * | 9/2007 | Sasaki | 396/148 |
| 2008/0024615 | A1 * | 1/2008 | Alvarez et al. | 348/211.7 |
| 2009/0109429 | A1 | 4/2009 | Scott et al. | |
| 2009/0109431 | A1 | 4/2009 | Delmonico et al. | |
| 2009/0115726 | A1 * | 5/2009 | Van Zon et al. | 345/161 |

* cited by examiner

*Primary Examiner* — Mehrdad Dastouri
*Assistant Examiner* — Kristin Dobbs
(74) *Attorney, Agent, or Firm* — Barclay Damon, LLP

(57) ABSTRACT

A method and system for steering an insertion tube of a video inspection device is disclosed for detecting a precise steering request made by displacing a pointing device from its stationary position and then returning the pointing device to or near its stationary position within a short interval of time. This precise steering request is then used by the video inspection device to steer the insertion tube a fixed distance in a direction based on the direction of the displacement of the pointing device for precise positioning of the camera head of the insertion tube.

21 Claims, 4 Drawing Sheets

METHOD AND SYSTEM FOR STEERING AN INSERTION TUBE OF A VIDEO INSPECTION DEVICE

BACKGROUND OF THE INVENTION

The subject matter disclosed herein relates to video inspection devices and, more particularly, to methods and systems for steering an insertion tube of a video inspection device.

Video inspection devices, such as video borescopes/endoscopes, can be used to inspect an object to identify and analyze anomalies (e.g., cracks) that may have resulted from damage to, or wear of, the object. For example, a video inspection device can be used to inspect the blade of a turbine engine to identify any anomalies that may have formed to determine if any repair or maintenance is required. In order to make that assessment, it is often necessary to obtain and display video images showing the anomaly and then to use those video images to report and analyze the anomaly, including using the video images to make highly accurate dimensional measurements.

For many inspections conducted with a video inspection device, at least a portion of the object to be inspected is inaccessible and cannot be viewed without the use of an insertion tube with a camera head at its distal end that can be positioned proximate to the portion of the object to be inspected. During an inspection, an inspector can use a pointing device (e.g., a joystick) of the video inspection device to steer the insertion tube by controlling a plurality of articulation cables that move a bending neck located at the distal end of the insertion tube to position the camera head to obtain video images of anomalies on the object. These video images can be displayed on a video display of the video inspection device during the inspection and saved for further analysis. In many instances, it is desirable to steer the insertion tube to precisely position the camera head such that the anomaly is in the center of the video image obtained by the camera head to facilitate subsequent reporting and analysis of the anomaly. For example, centering the anomaly in the video images typically provides optimal illumination of the anomaly and decreases the risk of having a portion of the anomaly not captured in the video image.

While the coarse steering of the bending neck to position the camera head proximate to the anomaly can often be accomplished with little difficulty by the inspector, precise steering of the bending neck required to center the anomaly in a video image is more difficult to accomplish as the pointing device cannot easily be used to steer the insertion tube and camera head to a precise position. The inability of the video inspection device to easily provide for precise steering of the insertion tube can frustrate the inspector and compromise the quality of the reporting and analysis of the anomaly if the anomalies are not properly positioned in the video images.

The discussion above is merely provided for general background information and is not intended to be used as an aid in determining the scope of the claimed subject matter.

BRIEF DESCRIPTION OF THE INVENTION

A method and system for steering an insertion tube of a video inspection device is disclosed for detecting a precise steering request made by displacing a pointing device from its stationary position and then returning the pointing device to or near its stationary position within a short interval of time. This precise steering request is then used by the video inspection device to steer the insertion tube a fixed distance in a direction based on the direction of the displacement of the pointing device for precise positioning of the camera head of the insertion tube. An advantage that may be realized in the practice of some of the disclosed embodiments of the steering method and system is that, during an inspection of an object, an inspector may more easily precisely position the camera head to obtain video images of anomalies of the object centered in the video image, improving the reporting and analysis of the anomalies.

In one embodiment, a system for steering an insertion tube of a video inspection device displaying a video image of an object obtained by the insertion tube on a video display is disclosed. The system includes a pointing device for outputting signals representative of the coordinates of the position of the pointing device, wherein a stationary position of the pointing device is the position at which the pointing device does not move the insertion tube, a timer for determining the elapsed time between when a distance of a displacement of the pointing device from the stationary position exceeded a second displacement zone threshold distance and when the distance of the displacement of the pointing device from the stationary position returns to a point less than a first displacement zone threshold distance, a processor for determining whether the elapsed time is less than a displacement time threshold, and an articulation cable actuator for, if the elapsed time is less than a displacement time threshold, moving a set of articulation cables of the insertion tube by a fixed distance in a direction based on the direction of the displacement of the pointing device from the stationary position that exceeded the second displacement zone threshold distance.

In another embodiment, a method for using a pointing device to steer an insertion tube of a video inspection device displaying a video image of an object obtained by the insertion tube on a video display is disclosed. The method includes the steps of determining the coordinates of the position of the pointing device, wherein a stationary position of the pointing device is the position at which the pointing device does not move the insertion tube, determining the elapsed time between when a distance of a displacement of the pointing device from the stationary position exceeded a second displacement zone threshold distance and when the distance of the displacement of the pointing device from the stationary position returns to a point less than a first displacement zone threshold distance, determining whether the elapsed time is less than a displacement time threshold, and if the elapsed time is less than the displacement time threshold, moving a set of articulation cables of the insertion tube by a fixed distance in a direction based on the direction of the displacement of the pointing device from the stationary position that exceeded the second displacement zone threshold distance.

In yet another embodiment, the method includes the steps of determining the coordinates of the position of the pointing device, wherein a stationary position of the pointing device is the position at which the pointing device does not move the insertion tube, determining the elapsed time between when a distance of a displacement of the pointing device from the stationary position exceeded a first displacement zone threshold distance and when the distance of the displacement of the pointing device from the stationary position returns to a point less than the first displacement zone threshold distance, determining whether the elapsed time is less than a displacement time threshold, determining whether the displacement of the pointing device from the stationary position exceeded a second displacement zone threshold distance, wherein the second displacement zone threshold distance is greater than the first displacement zone threshold distance, and if the displacement of the pointing device from the stationary position exceeded a second displacement zone threshold distance and the elapsed time is less than the displacement time threshold, moving a set of articulation cables of the insertion tube by a fixed distance in a direction based on the direction of the displacement of the pointing device from the stationary position that exceeded the second displacement zone threshold distance.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
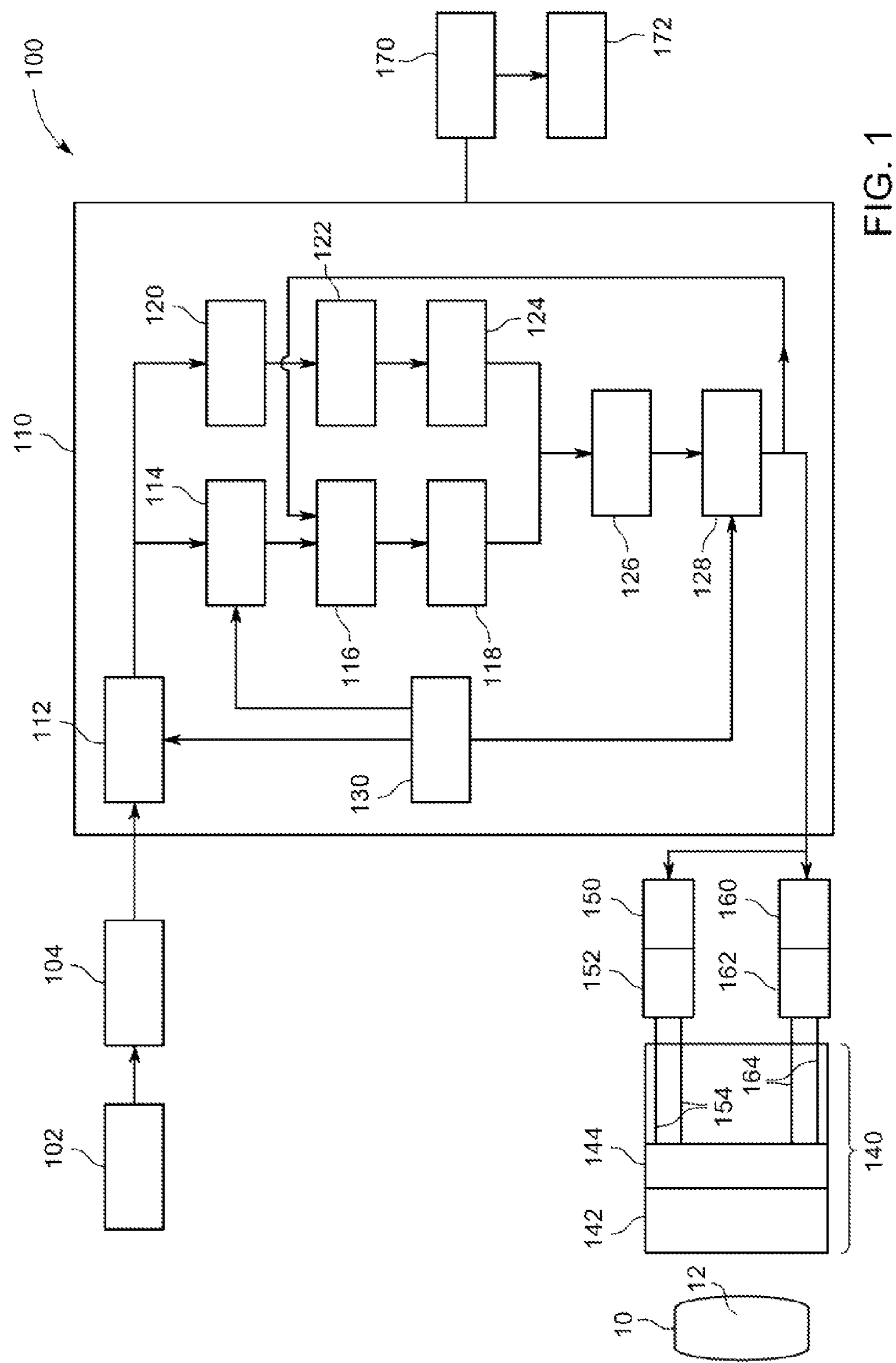
FIG. 1 is block diagram of an exemplary steering system for an exemplary video inspection device in one embodiment of the invention.

FIG. 1 is block diagram of an exemplary steering system for an exemplary video inspection device 100 in one embodiment of the invention. A pointing device 102 is used to steer an insertion tube 140 of the video inspection device 100 to position the camera head 142 to obtain video images of an anomaly 12 on an object 10. In one mode of steering, the steering system of the video inspection device 100 uses the distance and direction of the displacement of the pointing device 102 from its stationary (or center or resting) position to determine the speed and direction to steer the insertion tube 140 and its camera head 142. When the pointing device 102 is located at its stationary position (e.g., no displacement from the center or resting position), the steering system does not move the insertion tube 140 and its camera head 142. When the pointing device 102 is displaced from its stationary position a relatively small distance, the steering system moves the insertion tube 140 and its camera head 142 slowly in the direction of the displacement. When the pointing device 102 is displaced from its stationary position a relatively large distance, the steering system moves the insertion tube 140 and its camera head 142 quickly in the direction of the displacement.

In the embodiment disclosed in FIG. 1, a joystick is used as the pointing device 102, where the position of the pointing device 102 on X and Y axes is monitored by sensors, which output a voltage representative of the coordinates of the position of the pointing device 102. It will be understood other types of pointing devices 102 can be used besides a joystick (e.g., mouse, touch screen, keyboard, trackball, etc.). The pointing device 102 may have a range of analog output voltage values (e.g., 0.0V to 3.0V) covering the entire range of coordinates of possible positions on the X and Y axes from $-X_{Pmax}$, $-Y_{Pmax}$ (0.0V, 0.0V) to $+X_{Pmax}$, $+Y_{Pmax}$ (3.0V, 3.0V), including the stationary position, $X_{Ps}$, $Y_{Ps}$ (1.5V, 1.5V). The pointing device 102 can be connected to an analog-to-digital (A/D) converter 104 that converts the analog signals produced by the pointing device 102 to digital signals. It will be understood that an A/D converter 104 is not necessary if the pointing device 102 can output digital signals.

In one embodiment, the digital signals from the pointing device 102 are sent to a processor 110 (e.g., digital signal processor, microcomputer, microcontroller, etc.). The digital signals can be numerical values (e.g., 0 ($-X_{Pmax}$, $-Y_{Pmax}$), 2,048 ($X_{Ps}$, $Y_{Ps}$), 4,096 ($+X_{Pmax}$, $+Y_{Pmax}$)) representative of the coordinates of the position ($X_P$, $Y_P$) of the pointing device 102. The video inspection device 100 can be configured to provide the coordinates of the position ($X_P$, $Y_P$) of the pointing device 102 every 10 ms (i.e., 100 times per second), resulting in 100 samples of the X position and 100 samples of the Y position every second. Unwanted electrical noise in the signals output from the pointing device 102 can result in inaccurate coordinate data, which can detrimentally affect the performance of the video inspection device 100 by introducing jitter or shaking in the video images obtained during an inspection. For example, if the coordinates for a pointing device 102 at its stationary position should be X=2,048, Y=2048, but electrical noise causes the coordinates to be output at a higher value (e.g., X=2,248, Y=2,248), the video inspection device 100 will steer the insertion tube 140 assuming that the pointing device 102 had been displaced by the inspector.

To reduce the effect of the electrical noise, the video inspection device 100 can include a noise filter module 112 for receiving the digital signals from the pointing device 102 representative of the coordinates of the position ($X_P$, $Y_P$) of the pointing device 102. The noise filter module 112 can use a windowed average filter on the samples of each axis to reduce the effect of electrical noise as per the following equations applied to the position coordinates of each new sample ($X_{Pnew}$, $Y_{Pnew}$), resulting in a filtered position coordinate ($X_{Pf}$, $Y_{Pf}$)):

$$X_{Pf}=X_{Pf}+(X_{Pnew}-X_{Pf})/W_S \quad (1)$$

$$Y_{Pf}=Y+(Y_{Pnew}-Y_{Pf})/W_S \quad (2)$$

where $W_S$ is the weight assigned to each sample.

As can be seen from equation (1) when applied to four consecutive samples for the X axis of the pointing device 102 ($X_{Pnew1}$=2,048, $X_{Pnew2}$=2,048, $X_{Pnew3}$=2248 (increase of +200 caused by electrical noise), $X_{Pnew4}$=2,048), the use of a sample weight greater than one (e.g., $W_S$=4) can reduce the effect of electrical noise in the filtered samples ($X_{Pf1}$=2,048, $X_{Pf2}$=2,048, $X_{Pf3}$=2098 (increase of +50 caused by electrical noise), $X_{Pf4}$=2,087 (increase of +39 caused by electrical noise)), smoothing out any jitter caused by the electrical noise. While the use of a higher sample weight ($W_S$) can further minimize the effect of electrical noise by providing a higher degree of filtering, the higher sample weight ($W_S$) will also reduce the responsiveness of the video inspection device 100 as it will take more samples of the coordinates of the pointing device 102 at a new position to move the insertion tube 140 at the speed desired. For example, if the inspector displaced the pointing device 102 from its stationary position ($X_{Ps}$=2,048) to a new position ($X_{Pnew}$=2,248) to steer the insertion tube 140 at a desired speed commensurate with that distance of displacement, with a sample weight of four ($W_S$=4), it will take several new samples at that new position for the filtered sample ($X_{Pf}$) to equal the coordinate of the new position (e.g., ($X_{Pnew1}$=$X_{Pnew2}$=$X_{Pnew3}$=$X_{Pnew4}$=2,248), ($X_{Pf1}$=2,098, $X_{Pf2}$=2,135, $X_{Pf3}$=2163, $X_{Pf4}$=2184, etc.)) and produce the desired speed of steering. The sample weight ($W_S$) can be provided to the noise filter module 112 by the calibration and parameter data module 130. The filtered coordinates ($X_{Pf}$, $Y_{Pf}$) of the pointing device 102 are then processed by the processor 110 to determine the required steering of the insertion tube 100.

In one embodiment, the filtered coordinates ($X_{Pf}$, $Y_{Pf}$) of the pointing device 102 are received by a pointing device position mapping module 114, which, using conventional techniques, maps the distance and displacement of the pointing device 102 from its stationary position to determine a target insertion tube position value using data about the pointing device 102 and the insertion tube 140 provided by the calibration and parameter data module 130. The target insertion tube position value can be the target position of the camera head 142, the bending neck 144, or some other component of the insertion tube 140 (e.g., an articulation cable actuator). The target insertion tube position value can then be received by the insertion tube position comparing module 116, which, using conventional techniques, compares the target insertion tube position value to the current insertion tube position value to determine an insertion tube position error value (i.e., the difference between the target insertion tube position to the current insertion tube position).

The insertion tube position error value can then be received by the insertion tube position calculation module 118, which, using conventional techniques, checks and modifies the insertion tube position error value based on the data provided by the calibration and parameter data module 130 to meet performance requirements for the video inspection device 100. The insertion tube position calculation module 118 determines a calculated insertion tube steering value, which provides the calculated amount of steering of the insertion tube 140 in the X and Y directions required to move from the current position of the insertion tube 140 to the target position of the insertion tube 140. The calculated insertion tube steering value can then be passed to an insertion tube steering summing module 126, which can sum the calculated insertion tube steering value along with other insertion tube steering values provided from any other modules to determine a composite insertion tube steering value, which provides the actual distance that the insertion tube 140 will be steered in the X and Y directions.

The composite insertion tube steering value can then be passed to limit checking module 128, which, using conventional techniques, confirms that moving a set of articulation cables 154, 164 of the insertion tube 140 based on the insertion tube steering value will not exceed any distance or speed limits for the insertion tube 140 based on the data provided by the calibration and parameter data module 130. If the composite insertion tube steering value does not exceed any limits, the processor 110 sends the composite insertion tube steering value (e.g., the changes (deltas) in the X and Y axes) to the first (X axis) and second (Y-axis) of an articulation cable actuator (e.g., servo motors 150, 160, which, using conventional techniques, control the first and second cams 152, 162) for moving the first and second set of articulation cables 154, 164 which control the bending neck 144 of the insertion tube 140 to position the camera head 142 with respect to the anomaly 12 on the object 10 under inspection. The processor 110 can communicate with a video processor 170, which can output video images of the object 10 on a video display 172.

As discussed, the use of this conventional steering system alone can present difficulties for an inspector when trying to use the pointing device 102 to produce precise steering of the insertion tube 140 required to center the anomaly 12 in a video image. For example, in some steering systems, it may not be possible to displace the pointing device 102 from its stationary position a small enough distance to produce the precise steering required. In other instances, it may not be possible to displace the pointing device 102 from its stationary position at a predictable or consistent distance to produce the precise steering required. In order to provide this precise steering of the insertion tube 140, the video inspection device 100 can also incorporate modules and techniques to detect a precise steering request made by the inspector. This precise steering request is then used by the video inspection device 100 to move the articulation cable actuator of the insertion tube 140 a fixed distance in the direction of the displacement of the pointing device 102 for precise positioning of the camera head 142 of the insertion tube 140. As shown in FIG. 1, the exemplary steering system of the exemplary video inspection device 100 can have a precise steering request detection module 120 for receiving the filtered coordinates ($X_{Pf}$, $Y_{Pf}$) of the pointing device 102. In one embodiment, a precise steering request can be made by the inspector by displacing the pointing device 102 from its stationary position and then returning the pointing device 102 to or near its stationary position within a short interval of time.

Figure 2:
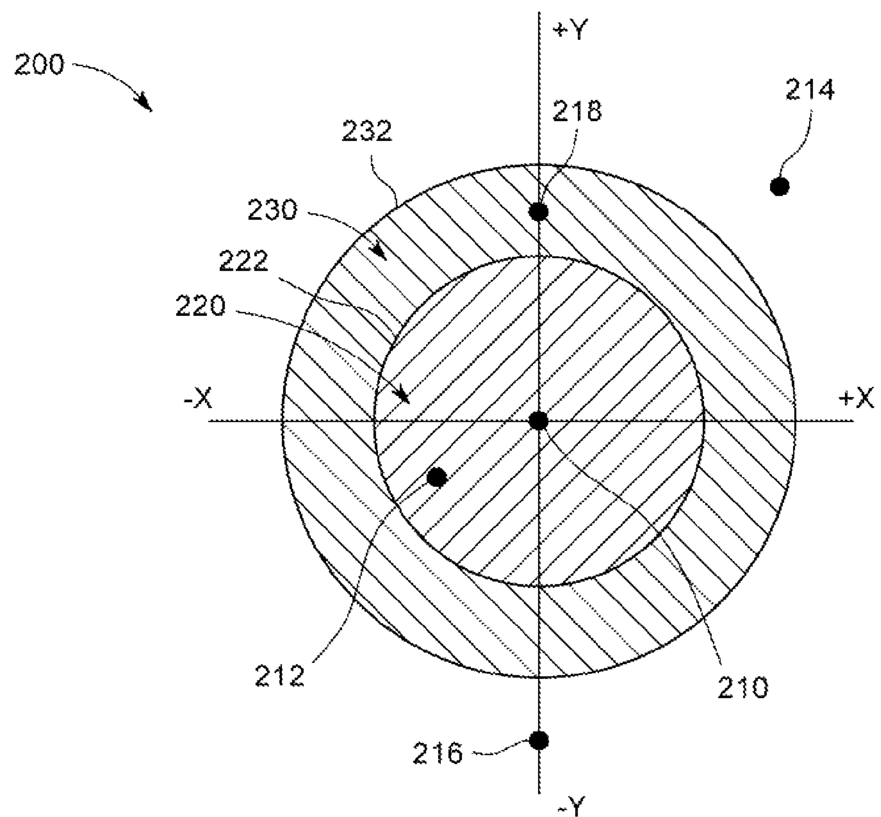
FIG. 2 is an exemplary map of the displacement of an exemplary pointing device in the video inspection device of FIG. 1.

FIG. 2 is an exemplary map 200 of the displacement of an exemplary pointing device 102 (e.g., a joystick) in the video inspection device 100 of FIG. 1. In one embodiment, the detection of a precise steering request can be made based on the displacement of the pointing device 102 from its stationary position 210 with respect to a first displacement zone 220 concentrically surrounding the stationary position 210, and a second displacement zone 230, concentrically surrounding the first displacement zone 220. The first displacement zone 220 can be between the stationary position 210 and a first displacement zone threshold distance 222, while the second displacement zone 230 is the area between the first displacement zone threshold distance 222 and a second displacement zone threshold distance 232, which is at a greater displacement distance from the stationary position 210 than the first displacement zone threshold distance 222. The values defining the displacement zones 220, 230 and the displacement zone threshold distances 222, 232 can be provided to the precise steering request detection module 120 by the calibration and parameter data module 130.

In one embodiment, a precise steering request is detected if, as shown in displacement points 214 and 216, the pointing device 102 is displaced a distance greater than the second displacement zone threshold distance 232 and then returns back to a displacement distance less than the first displacement zone threshold distance 222 (e.g., slightly less than the first displacement zone threshold distance 222 or at the stationary position 210) in a time less than a displacement time threshold (e.g., 0.25 seconds or less). The precise steering request detection module 120 can include a timer (or the timer can be separate) for determining the elapsed time between when the pointing device 102 is displaced outside of the first displacement zone 220 (i.e., at a displacement distance exceeding the first displacement zone threshold distance 222) and when the pointing device returns to the first displacement zone 220 (i.e., at a displacement distance less than the first displacement zone threshold distance 222). Referring to FIG. 2, a precise steering request would not be detected if, as shown in displacement point 212, the pointing device 102 is displaced a distance less than the first displacement zone threshold distance 222, or, as shown in displacement point 218, the pointing device 102 is displaced a distance less than the second displacement zone threshold distance 232. A precise steering request would not be detected even if the pointing device 102 had displacements as in points 214 and 216 if the elapsed time between when the pointing device 102 is displaced outside of the first displacement zone 220 (i.e., at a displacement distance exceeding the first displacement zone threshold distance 222) and when the pointing device 102 returns to the first displacement zone 220 (i.e., at a displacement distance less than the first displacement zone threshold distance 222) was greater than the displacement time threshold. The displacement time threshold can be provided to the precise steering request detection module 120 by the calibration and parameter data module 130 and can be adjusted to modify the sensitivity of the precise steering request.

Figure 3:
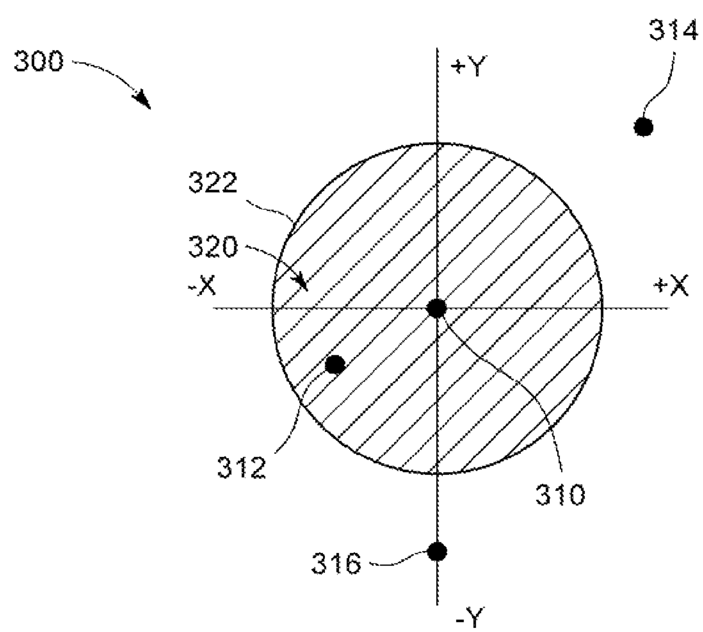
FIG. 3 is another exemplary map of the displacement of an exemplary pointing device in the video inspection device of FIG. 1.
Figure 4:
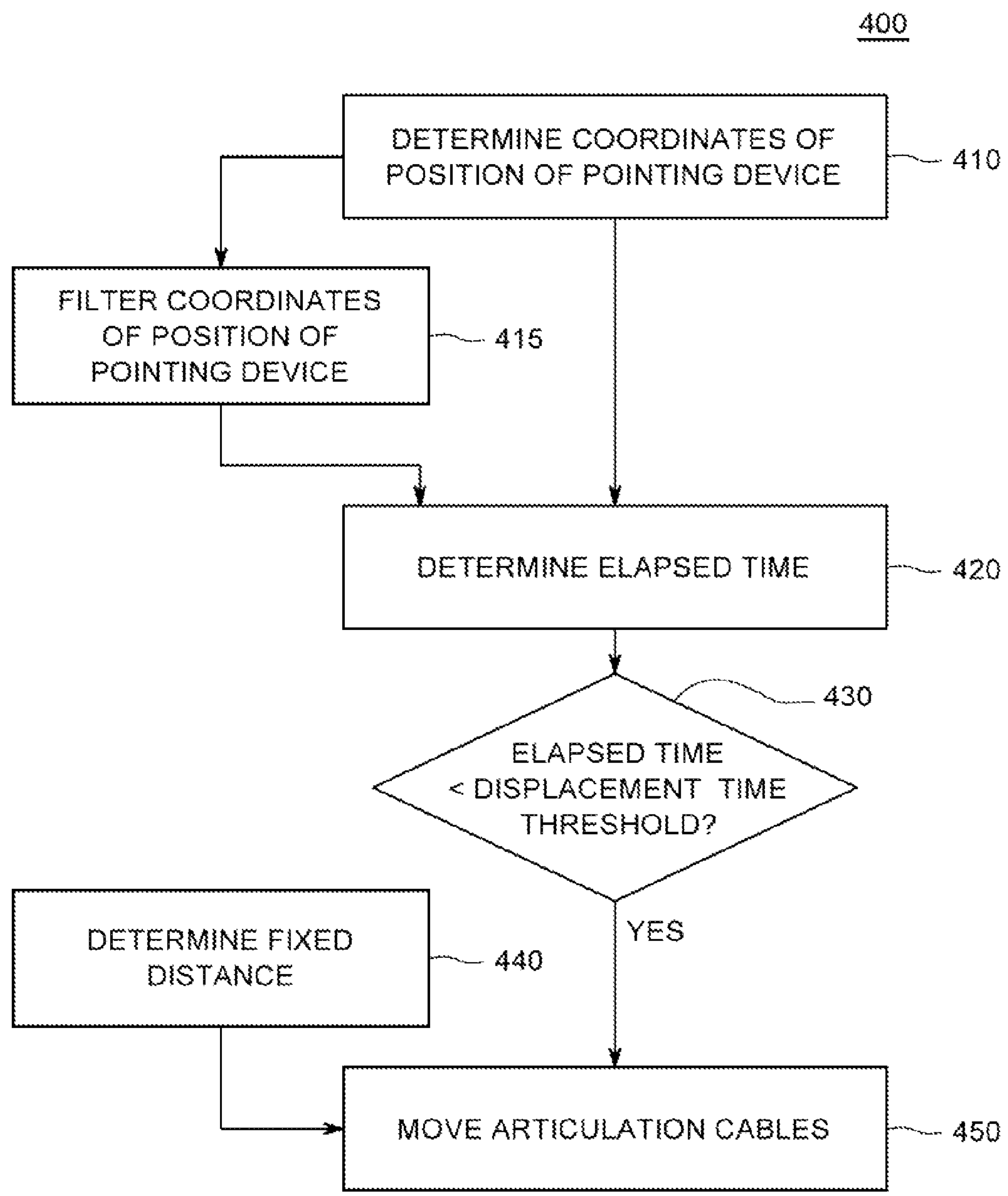
FIGS. 4 and 5 are flowcharts showing exemplary methods for using a pointing device to steer an insertion tube of a video inspection device.
Figure 5:
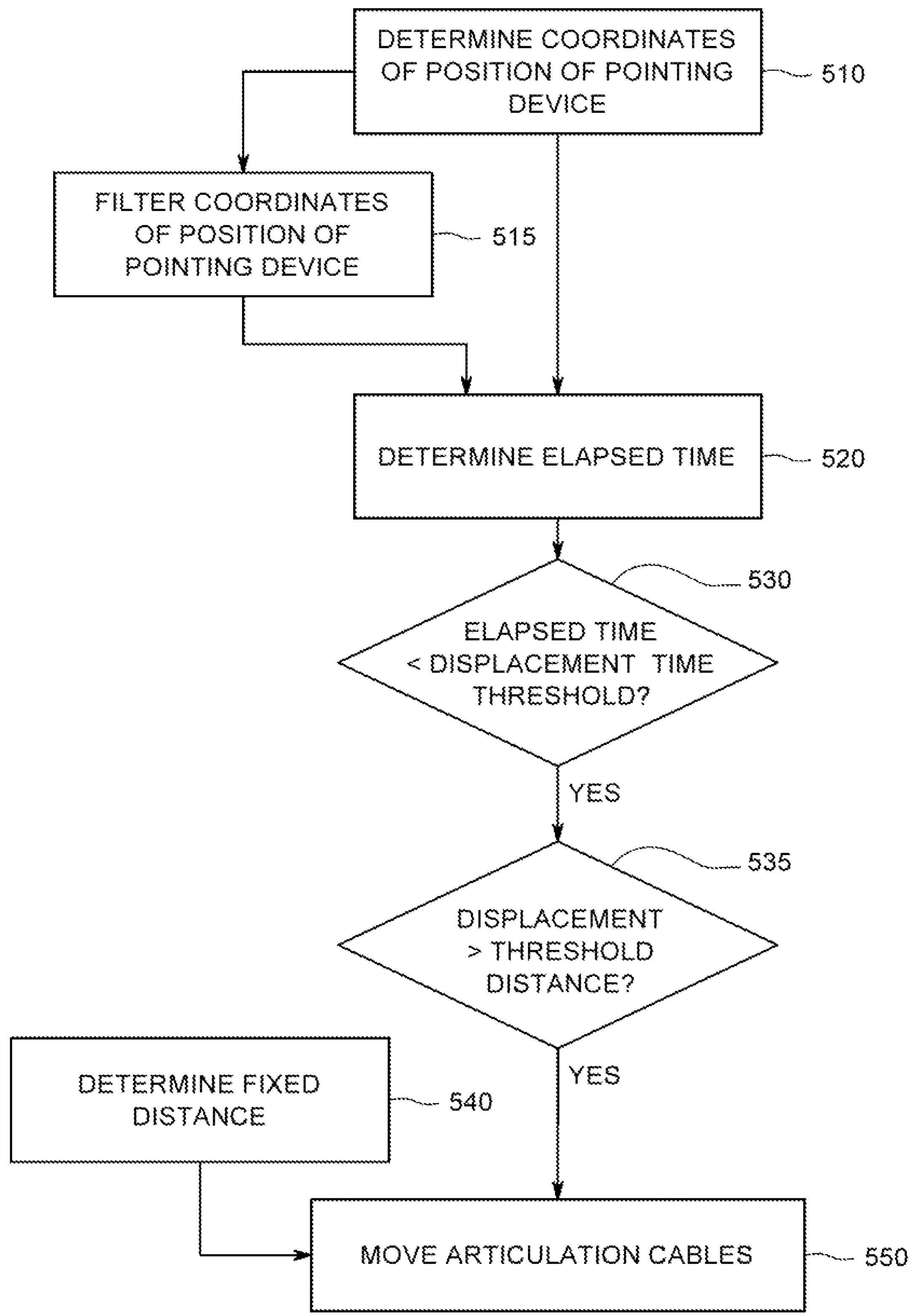

The use of two displacement zones 220, 230 and two displacement zone threshold distances 222, 232 in FIG. 2 helps to eliminate any instability in the detection of a precise steering request as the second displacement zone 230 operates as a hysteresis band to handle displacements such as point 218 that are proximate the boundary of the first displacement zone 220. FIG. 3 is another exemplary map 300 of the displacement of an exemplary pointing device 102 (e.g., a joystick) in the video inspection device 100 of FIG. 1. In one embodiment, the detection of a precise steering request can be made based on the displacement of the pointing device 102 from its stationary position 310 with respect to a single displacement zone 320 concentrically surrounding the stationary position 210. The displacement zone 320 can be between the stationary position 310 and a displacement zone threshold distance 322. The values defining the displacement zone 320 and the displacement zone threshold distance 322 can be provided to the precise steering request detection module 120 by the calibration and parameter data module 130.

In one embodiment, a precise steering request is detected if, as shown in displacement points 314 and 316, the pointing device 102 is displaced a distance greater than the displacement zone threshold distance 322 and then returns back to a displacement distance less than the displacement zone threshold distance 322 (e.g., slightly less than the displacement zone threshold distance 322 or at the stationary position 310) within a short interval of time (e.g., 0.25 seconds or less). The precise steering request detection module 120 can include a timer (or the timer can be separate) for determining the elapsed time between when the pointing device 102 is displaced outside of the displacement zone 320 (i.e., at a displacement distance exceeding the displacement zone threshold distance 322) and when the pointing device returns to the displacement zone 320 (i.e., a displacement distance less than the displacement zone threshold distance 322). Referring to FIG. 3, a precise steering request would not be detected if, as shown in displacement point 312, the pointing device 102 is displaced a distance less than the displacement zone threshold distance 322. A precise steering request would not be detected even if the pointing device 102 had displacements as in points 314 and 316 if the elapsed time between when the pointing device 102 is displaced outside of the displacement zone 320 (i.e., at a displacement distance greater than the displacement zone threshold distance 322) and when the pointing device 102 returns to the displacement zone 320 (i.e., a displacement distance less than the displacement zone threshold distance 322) was greater than the displacement time threshold. The displacement time threshold can be provided to the precise steering request detection module 120 by the calibration and parameter data module 130 and can be adjusted to modify the sensitivity of the precise steering request.

Inspector actions such as bumping or nudging the pointing device 102 in a rapid fashion or similar gestures should be recognized as precise steering requests. Returning to FIG. 1, if a precise steering request is detected by the precise steering request detection module 120, a plurality of precise steering request counters (e.g., counter for +X, counter for −X, counter for +Y, counter for −Y) in the precise steering request counter module 122 are incremented by integers or fractions based on the direction of the displacement of pointing device 102 in the precise steering request. For example, if the displacement of the pointing device 102 to displacement points 214, 314 was detected as a precise steering request, since the diagonal displacement was in the positive X and positive Y directions, the +X and +Y precise steering request counters would be incremented. Similarly, if the vertical displacement of the pointing device 102 to displacement points 216, 316 was detected as a precise steering request, since the displacement was in the negative Y direction, only the −Y precise steering request counter would be incremented.

If one or more precise steering request counters have non-zero values, a precise steering request position module 124 can determine the fixed distance that the insertion tube 140 will be steered in the X and Y directions based on the direction of the precise steering request displacement. In one embodiment, a precise steering request in one or more directions (+X, −X, +Y, −Y) can move the articulation cable actuator of the insertion tube 140 (i.e., including the camera head 142 and bending neck 144) a fixed distance that will result in a movement of the video image of a certain percentage of (e.g., 5%), or distance on (e.g., 0.25 in. (6.35 mm)) the video display 172 based on the data provided by the calibration and parameter data module 130 for the insertion tube 140 and the video display 172. For example, if the displacement of the pointing device 102 to displacement points 214, 314 was detected as a precise steering request, since the diagonal displacement was in the positive X and positive Y directions, the +X and +Y precise steering request counters would be incremented, this could result in the camera head 142 being steered to provide a video image that moves 5% of the video display 172 in both the +X and +Y directions. The fixed distance that the insertion tube 140 is steered is based on the direction of the displacement of the pointing device and not based on the distance of displacement, eliminating the need for the inspector to be have a precise movement of the pointing device 102 to move the insertion tube 140 a precise distance.

The number of precise steering request counters can limit the number of directions for precise steering requests and directions of moving a set of articulation cables of the insertion tube 140. In another embodiment, the precise steering request counter module 122 can have precise steering request counters for 0° (north), 45° (northeast), 90° (east), 135° (southeast), 180° (south), 225° (southwest), 270° (west), 315° (northwest). If the displacement of the pointing device 102 to displacement points 214, 314 was detected as a precise steering request, the 45° (northeast) precise steering request would be incremented. Similarly, if the vertical displacement of the pointing device 102 to displacement points 216, 316 was detected as a precise steering request, the 180° (south) precise steering request counter would be incremented. In another embodiment using fractional counters, the precise steering request can be in any direction or angle from 0° to 360°. The counters (X and Y) can be calculated using the following equations:

$$X=\sin(\text{pointing device displacement angle}) \quad (3)$$

$$Y=\cos(\text{pointing device displacement angle}) \quad (4)$$

The precise steering request position module 124 can provide a precise steering request steering value for the desired steering and pass it to the insertion tube steering summing module 126 as discussed above, which can determine a composite insertion tube steering value, which provides the actual distance that the insertion tube 140 will be steered in the X and Y directions by moving the articulation cable actuator. The composite insertion tube steering value can be set equal to the precise steering request steering value or can be the sum of the precise steering request steering value and the calculated insertion tube steering value discussed previously.

In view of the foregoing, embodiments of the methods and systems for steering an insertion tube 140 of a video inspection device 100 provide video images to an inspector that is performing an inspection. A technical effect is to improve the inspection process by allowing an inspector to more easily precisely position the camera head 142 to obtain video images of anomalies 12 of the object 10 centered in the video image, improving the reporting and analysis of the anomalies 12.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for steering a camera head mounted to a bending neck of an insertion tube of a video inspection device displaying a video image of an object obtained by the insertion tube on a video display, the system comprising:

a pointing device for outputting signals representative of the coordinates of the position of the pointing device, wherein a stationary position of the pointing device is the position at which the pointing device does not move the insertion tube;

a timer for determining the elapsed time between when a distance of a displacement of the pointing device from the stationary position exceeded a second displacement zone threshold distance and when the distance of the displacement of the pointing device from the stationary position returns to a point less than a first displacement zone threshold distance, wherein the first displacement zone threshold distance is an outer bound of a first displacement zone surrounding the stationary position and the second displacement zone threshold distance is an outer bound of a second displacement zone surrounding the first displacement zone, and wherein the second displacement zone threshold distance is greater than the first displacement zone threshold distance;

a processor for determining whether the elapsed time is less than a displacement time threshold; and an articulation cable actuator for, if the elapsed time is less than the displacement time threshold, moving a set of bending-neck articulation cables of the insertion tube by a fixed distance in a direction based on the direction of the displacement of the pointing device from the stationary position that exceeded the second displacement zone threshold distance.

2. The system of claim 1, wherein the fixed distance is not based on the distance of the displacement of the pointing device from the stationary position that exceeded the second displacement zone threshold distance.

3. The system of claim 1, wherein the fixed distance is determined based on the movement of the set of bending-neck articulation cables of the insertion tube that will result in a movement of the video image of a certain percentage of the video display.

4. The system of claim 1, wherein the fixed distance is determined based on the movement of the set of bending-neck articulation cables of the insertion tube that will result in a movement of the video image of a certain distance on the video display.

5. The system of claim 1, wherein the displacement time threshold is 0.25 seconds or less.

6. A method for using a pointing device to steer a camera head mounted to a bending neck of an insertion tube of a video inspection device displaying a video image of an object obtained by the insertion tube on a video display, the method comprising the steps of:

determining the coordinates of the position of the pointing device, wherein a stationary position of the pointing device is the position at which the pointing device does not move the insertion tube;

determining the elapsed time between when a distance of a displacement of the pointing device from the stationary position exceeded a second displacement zone threshold distance and when the distance of the displacement of the pointing device from the stationary position returns to a point less than a first displacement zone threshold distance, wherein the first displacement zone threshold distance is an outer bound of a first displacement zone surrounding the stationary position and the second displacement zone threshold distance is an outer bound of a second displacement zone surrounding the first displacement zone, and wherein the second displacement zone threshold distance is greater than the first displacement zone threshold distance;

determining whether the elapsed time is less than a displacement time threshold; and if the elapsed time is less than the displacement time threshold, moving a set of bending-neck articulation cables of the insertion tube by a fixed distance in a direction based on the direction of the displacement of the pointing device from the stationary position that exceeded the second displacement zone threshold distance.

7. The method of claim 6, wherein the fixed distance is not based on the distance of the displacement of the pointing device from the stationary position that exceeded the second displacement zone threshold distance.

8. The method of claim 6, wherein the fixed distance is determined based on the movement of the set of bending-neck articulation cables of the insertion tube that will result in a movement of the video image of a certain percentage of the video display.

9. The method of claim 6, wherein the fixed distance is determined based on the movement of the set of bending-neck articulation cables of the insertion tube that will result in a movement of the video image of a certain distance on the video display.

10. The method of claim 6, wherein the displacement time threshold is 0.25 seconds or less.

11. The method of claim 6, further comprising the step of filtering the coordinates of the position of the pointing device to remove electrical noise using windowed average filtering.

12. A method for using a pointing device to steer a camera head mounted to a bending neck of an insertion tube of a video inspection device displaying a video image of an object obtained by the insertion tube on a video display, the method comprising the steps of:

determining the coordinates of the position of the pointing device, wherein a stationary position of the pointing device is the position at which the pointing device does not move the insertion tube;

determining the elapsed time between when a distance of a displacement of the pointing device from the stationary position exceeded a first displacement zone threshold distance and when the distance of the displacement of the pointing device from the stationary position returns to a point less than the first displacement zone threshold distance, wherein the first displacement zone threshold distance is an outer bound of a first displacement zone surrounding the stationary position and the second displacement zone threshold distance is an outer bound of a second displacement zone surrounding the first displacement zone, and;

determining whether the elapsed time is less than a displacement time threshold;

determining whether the displacement of the pointing device from the stationary position exceeded a second displacement zone threshold distance, wherein the second displacement zone threshold distance is greater than the first displacement zone threshold distance; and if the displacement of the pointing device from the stationary position exceeded a second displacement zone threshold distance and the elapsed time is less than the displacement time threshold, moving a set of bending-neck articulation cables of the insertion tube by a fixed distance in a direction based on the direction of the displacement of the pointing device from the stationary position that exceeded the second displacement zone threshold distance.

13. The method of claim 12, wherein the fixed distance is not based on the distance of the displacement of the pointing device from the stationary position that exceeded the second displacement zone threshold distance.

14. The method of claim 12, wherein the fixed distance is determined based on the movement of the set of bending-neck articulation cables of the insertion tube that will result in a movement of the video image of a certain percentage of the video display.

15. The method of claim 12, wherein the fixed distance is determined based on the movement of the set of bending-neck articulation cables of the insertion tube that will result in a movement of the video image of a certain distance on the video display.

16. The method of claim 12, wherein the displacement time threshold is 0.25 seconds or less.

17. The method of claim 12, wherein the point less than the first displacement zone threshold distance is the stationary position.

18. The method of claim 12, further comprising the step of filtering the coordinates of the position of the pointing device to remove electrical noise using windowed average filtering.

19. The system of claim 1, wherein the first displacement zone threshold distance is an outer bound of a first displacement zone concentrically surrounding the stationary position and the second displacement zone threshold distance is an outer bound of a second displacement zone concentrically surrounding the first displacement zone.

20. The method of claim 6, wherein the first displacement zone threshold distance is an outer bound of a first displacement zone concentrically surrounding the stationary position and the second displacement zone threshold distance is an outer bound of a second displacement zone concentrically surrounding the first displacement zone.

21. The method of claim 12, wherein the first displacement zone threshold distance is an outer bound of a first displacement zone concentrically surrounding the stationary position and the second displacement zone threshold distance is an outer bound of a second displacement zone concentrically surrounding the first displacement zone.

* * * * *